United States Patent
Olivier

(10) Patent No.: US 6,623,953 B1
(45) Date of Patent: Sep. 23, 2003

(54) ENZYMATIC COMPOSITION AND METHOD FOR SEASONING WOOD

(75) Inventor: Henry Olivier, Wavre (BE)

(73) Assignee: ETS. Robert Stiernon S.A., Petit-Enghien (BE)

(*) Notice: Subject to any disclaimer, the term of this patent is extended or adjusted under 35 U.S.C. 154(b) by 0 days.

(21) Appl. No.: 09/869,656

(22) PCT Filed: Dec. 17, 1999

(86) PCT No.: PCT/BE99/00164

§ 371 (c)(1), (2), (4) Date: Jun. 29, 2001

(87) PCT Pub. No.: WO00/40382

PCT Pub. Date: Jul. 13, 2000

(30) Foreign Application Priority Data

Dec. 31, 1998 (EP) .............................................. 98124852
Jun. 25, 1999 (BE) .............................................. 9900444

(51) Int. Cl.⁷ .............................. C12S 3/00; B27K 5/00
(52) U.S. Cl. ...................... 435/267; 435/274; 435/277; 435/201; 435/202; 435/209; 435/200; 106/124.1; 144/335
(58) Field of Search ................................. 435/267, 274, 435/277, 201, 202, 209, 200; 106/124.1; 144/335

(56) References Cited

U.S. PATENT DOCUMENTS 2,119,234 A * 5/1938 Krebs et al. .................... 99/48
4,346,175 A   8/1982 Enfors et al. ................ 435/317

FOREIGN PATENT DOCUMENTS

| DE | 292 864 | 8/1991 |
| FR | 2421039 | 10/1979 |
| FR | 2705607 | * 2/1994 |
| FR | 2705607 | 12/1994 |

OTHER PUBLICATIONS http://us.expasy.org/cgi–bin/get–enzyme–entry–unprecise?3.2.1.– (listing enzymes within Glycosidase class), and http://us.expasy.org/cgi–bin/nicezyme.pl?3.2.1.4 (individual listing for cellulase), 2002.*

* cited by examiner

Primary Examiner—Francisco Prats
(74) Attorney, Agent, or Firm—Olson & Hierl, Ltd.

(57) ABSTRACT

The invention relates to an enzymatic composition and also to a method for seasoning wood, intended in particular for applications in the food industry. The method consists in immersing green wood in an aqueous solution comprising an enzymatic composition. The wood can subsequently be dried very rapidly in a drying facility. The invention makes it possible to improve the aromatic characteristics of the wood by eliminating certain substances judged to be undesirable due to their astringent nature or bitter nature, and transforming them into neutrally-tasting molecules.

18 Claims, No Drawings

ENZYMATIC COMPOSITION AND METHOD FOR SEASONING WOOD

The present invention relates to an enzymatic composition and an aqueous bath for seasoning or maturing green wood, and also to a method using this enzymatic composition or this bath.

Introduction

The use of wood as a material in construction, carpentry or cabinet-making presumes prior drying in order to dimensionally stabilize this wood. For cooperage, there are also organoleptic requirements.

For most industrial applications, this drying takes place in a drying facility at controlled temperature and humidity.

For other applications, in particular when the wood will subsequently be in contact with foods, the drying takes place naturally, outside, over quite long periods of time, with the aim of eliminating certain undesirable compounds. The duration of this natural drying, or ageing, can be varied depending on the final use. This drying can take up to 2 years in order to obtain good organoleptic qualities.

In the case of natural drying, the wood is colonized by a fungal flora which can transform certain compounds of the wood. These transformations of the wood cannot, however, be controlled. Naturally dried wood exhibits great variability of quality.

On the other hand, with artificial drying in a drying facility, these transformations do not occur and the wood thus dried is not suitable for food applications since this drying does not make it possible to eliminate certain undesirable molecules (such as toxic or bitter molecules).

STATE OF THE ART

EP 0 001 540 A relates to the use of microorganisms or of enzymes (pectinase or cellulase) with the aim of modifying the structure of wood intended for decoration, by controlling the temperature, the water content of the wood, and the $O_2$ and $CO_2$ content in the wood's environment. In this method, the wood is pretreated before inoculation, post treated in order to terminate the microbiological process, and then dried.

This complex method does not use immersion of the wood in an enzymatic preparation.

DD 292 864 A relates to improving the impregnability of the sapwood of resinous wood using an enzymatic preparation (pectinase, cellulase and hemicellulase), at the same time as an aqueous mineral preparation intended to superficially protect this wood.

This method does not relate to the duramen of the wood, or to species other than conifers, or to a food application.

FR 2 421 039 A relates to the conditioning of wood in a solid medium, using microorganisms, with a view to facilitating the fragmentation and then the agglomeration of the elements of the wood.

This method does not use immersion of the wood or an enzymatic preparation, and does not relate to application in the food industry.

FR 2 705 607 A relates to the use of microorganisms having $\alpha$-amylase and $\beta$-glucosidase activities, with a view to improving the organoleptic qualities of oak intended for cooperage. The microbiological process is carried out in the solid state using a fungal leaven. The process, which is supposed to reproduce the effects of natural drying/seasoning, specifies neither the duration of bringing the microorganisms into contact with the wood, nor the temperature, nor the microorganism content. It does not describe a method of immersion of the wood, nor an enzymatic preparation, and it applies only to species of oak.

DESCRIPTION OF THE INVENTION

The aim of the present invention is to provide a method for seasoning wood which allows, once it has been used, notably shortened drying of the wood. This method is suitable for food applications and conserves the dimensions of treated wood.

A subject of the invention is an enzymatic composition for drying wood, comprising mainly enzymes of the cellulase class, and also an aqueous bath for seasoning wood, comprising an endocellulase activity of between $1 \times 10^6$ and $100 \times 10^6$ ECU (preferably between $3 \times 10^6$ and $30 \times 10^6$ ECU) per $m^3$ of wood to be treated, xylanase activity of between $0.6 \times 10^6$ and $60 \times 10^6$ BXU (preferably between $2 \times 10^6$ and $20 \times 10^6$ BXU) per $m^3$ of wood to be treated, a $\beta$-mannanase activity of between $0.4 \times 10^6$ and $40 \times 10^6$ MNU (preferably between $1 \times 10^6$ and $10 \times 10^6$ MNU) per $m^3$ of wood to be treated and an $\alpha$-amylase activity of between $1 \times 10^6$ and $100 \times 10^6$ $_\alpha$TU (preferably between $3 \times 10^6$ and $30 \times 10^6$ $_\alpha$TU) per $m^3$ of wood to be treated.

A subject of the invention is also a method for seasoning wood, prior to drying, comprising a step of bringing the wood into contact with an aqueous bath comprising the composition according to the invention.

Particular embodiments of the invention are described in the dependent claims.

The enzymatic composition used may comprise enzymes of the exocellular or endocellular type. The enzymes may be of bacterial or fungal origin, or of any other possible origin.

DETAILED DESCRIPTION OF THE INVENTION

The wood to be treated, the water content of which has ideally been brought to between 25 and 45% by being rapidly passed through a drying facility, is immersed in a bath containing water or any other suitable solvent, and varying amounts of enzymes mainly of the hydrolase class (International Union of Biochemistry (IUB) class 3), chosen from enzymes of the cellulase type (also known under the name glucosidases) (IUB classification subclass 3.2). In addition, enzymes of the lipase (subclass 3.1), peroxidase (subclass 1.11.1), etc. type, and mixtures of these enzymes, may be added. Among cellulases which can be used for the present invention, mention may in particular be made of cellobiohydrolases, endoglucanases, $\beta$-glucosidases, hemicellulases, $\alpha$-amylases, and xylanases, endocellulases, $\beta$-mannanases, etc., without losing sight of the fact that the enzymes often have secondary activities besides their main activity.

Depending on whether neutral or acid cellulases are used, the pH of the bath is adjusted to between 3 and 8, preferably between 4 and 7. The temperature of the bath is kept constant at between 20 and 70° C., preferably between 30 and 50° C. After this treatment by immersion, which can last from 30 minutes to 2 weeks, preferably from 1 hour to 1 week, depending on the strength of the effect desired, on the mixture of enzymes used, on the volume to be treated, on the volume of the bath, on the nature of the wood treated and on the temperature and pH of the bath, the wood is then placed in the drying facility at controlled temperature and humidity in order to carry out conventional drying which makes it possible to attain a water content of 15 to 20% for use in cooperage, starting from a wood having a water content of between 25 and 45%, preferably between 30 and 40%, before the bringing into contact with the enzymatic preparation.

The method according to the invention has proved to enable hydrolysis of soluble ellagitannins naturally present in wood, firstly ellagitannins linked to parietal polysaccharides, and also diverse aromatic molecules (such as digallic acid or heteroside coumarins) which are transformed, by the method according to the invention, into neutrally tasting molecules.

The method according to the invention therefore makes it possible to improve the impact on taste of the wood extracts by eliminating a significant portion of the undesirable compounds (such as certain phenol compounds) and hydrolysing forms judged to be bitter or astringent. This is particularly important for wood subsequently coming into contact with foods (typically, wood for cooperage).

This method superficially modifies the ultrastructure of the wood. By electron microscopy, a decrease in the cell wall is noted over 1 mm. Over 1 to 3 mm, the pores of the cells are open. The effects of the process are felt up to a depth of approximately 5 mm.

The present invention also has the advantage of providing a rapid method for ageing wood, while at the same time respecting all of the physicochemical reactions linked to the natural drying of wood.

In addition, the invention has the advantage of providing a reproducible method for seasoning wood and of allowing better homogeneity of the quality of treated wood between different species of wood or species of wood of different origin, or between the various portions of the same tree. More constant physicochemical (in particular mechanical and aromatic) properties of the wood treated according to the invention are therefore obtained, with respect to wood dried naturally, this being independent of meteorological factors.

The method according to the invention also makes it possible, through a suitable choice of enzymes having more specific activities, to confer on the wood specific properties such as the expression of specific odours or flavours.

Materials and Methods

1. Origin of the Wood Samples

The oak samples consist of the heart-wood transformed into duramen, of trees from 110 to 150 years old, derived from homogeneous and suitably maintained areas of forest. Only the lower quarter of the trunk, generally constituting the wood for cooperage, is used for the study. The samples treated with the enzymatic composition according to the invention are simply dried in a drying facility (1 month, 40° C., with ventilation). The various randomly-taken samples are planed down to sawdust by crushing in liquid nitrogen, before being sieved so as to keep only the particles less than 250 $\mu$m in size. The samples are conserved after lyophilization, to be analysed within a period of 2 months. The species studied is Quercus petraea (Allier, France).

2. Preparation of Extracts and Control of Their Composition 1 g of sawdust (250 $\mu$m) is extracted with 100 ml of solvent (7:3 by volume acetone/water) for 12 h at room temperature on a shaking platform; the resulting extract is then filtered through a membrane, lyophilized and weighed.

100 $\mu$g of lyophilized extract are used to identify the major ellagitannins, with an LSIMS mass spectrometer.

1 mg of the extract is taken up with methanol/water (6:4) in order, to be analysed by HPLC coupled to a UV-detector and to an LSMIS mass spectrometer, according to the device developed by Vivas et al. (1995). The HPLC separation method is described in the following paragraph.

3. Assaying of Phenol Compounds 3.1. Coumarins

The coumarins are quantitatively extracted, by extraction with diethyl ether, from 20 ml of a wood extract. The organic phase is evaporated to dryness and the residue is taken up with methanol. The HPLC analysis is carried out using a Varian 5060 coupled with a spectrofluorometric detector (Kontron SFM23/B) and an Ultrasphere ODS column. The pure coumarins were supplied by Extrasynthèse (esculin, esculetin, scopoletin, ombelliferone, methylombelliferone) and Sigma (sporalen). The coumarins are observed by fluorescence (excitation 425 nm and emission 325 nm).

3.2. Ellagitannins 3.2.1. Reference Products

Vescalagin and castalagin are isolated and purified from the duramen of Q. robur, under the conditions described by Vivas et al. (1995). The various roburins (A–E) and grandinin originate from Scalbert (INA/INRA Thierval-Grignon).

3.2.2. Separation and Assaying of Ellagitannins by HPLC

The chromatographic technique for separating and assaying ellagitannins is in accordance with the method developed by Scalbert et al. (1990). The wood extracts are analysed by HPLC on an Ultrasphere ODS column. The detection is carried out at $\lambda$=280 nm.

3.2.3. Assaying of Total Ellagitannins a) Estimation of the Level of Total Phenol Compounds The richness of the wood extracts in total phenol compounds is estimated either by the method using the Folin-Ciocalteu reagent, or by measuring the absorbance at 280 nm of the extracts diluted 100-fold (Vivas et al., 1993). These two methods give results which are comparable but not specific for ellagitannins.

b) Reaction for Oxidation with Nitrous Acid

In this method proposed by Bate-Smith (1972), esters of hexahydroxyphenic acid and of glucose are oxidized with nitrous acid under a nitrogen stream. The reaction produces a blue coloration which is measured at 600 nm. The results are estimated in mg/g or mg/l of castalagin equivalent ($\epsilon_{600}$ nm: 983 $g^{-1}$).

c) Acid Degradation

The method proposed is adapted from that developed by Peng et al. (1991). It is based on the acid hydrolysis of ellagitannins, followed by assaying, by HPLC, of the released ellagic acid. The results are expressed in mg/g of castalagin equivalent, taking one mole of castalagin to give, under these conditions, one mole of ellagic acid (Peng et al., 1991).

4. Extraction and Assaying of Polysaccharides 4.1. Study of the Polysaccharide Fraction of the Control and Treated Samples 4.1.1. Extraction of Polysaccharides 139 g of dry sawdust are left to soak for 72 h on a shaking platform at room temperature. The solution is then filtered and centrifuged. The extract is then concentrated down to 500 ml.

4.1.2 Isolation of Polysaccharides

The extracts undergo 3 precipitations (one at 1:9 of water/ethanol at 95% vol., two at 1:5 of the same mixture). The precipitation is carried out at 3° C. for 12 h. Next, the fractions are lyophilized.

4.1.3. Partial Characterization

The precipitate has a frothy appearance, very pale in colour, slightly grey, which is probably a complex with the ellagitannins from which it is difficult to isolate the polysaccharide fraction.

4.1.4. Assaying Using a Chemical Method a) Assaying of Neutral Polysaccharides (nP)

The neutral polysaccharides are assayed using the sulphuric phenol method. The optical density is read at 490 nm and the results are expressed in mg/l of glucose equivalent.

b) Assaying of Acid Polysaccharides (aP)

The acid polysaccharides are assayed using the meta-phenylphenol method. The optical density is measured at 520 nm and the results are expressed in mg/l of galacturonic acid equivalent.

4.2. Extraction and Assaying of Polysaccharides from Wood 1 g of wood shavings derived from oak trees from various regions, the wood of which has a characteristic grain, is left to soak for 24 h in water at 20° C. on a shaking platform. The solution is collected by filtration and centrifuged. The sawdust recovered is then dried and left to soak once again, in a 5% sodium hydroxide solution, under the same conditions. The alkaline solution is also collected by filtration and centrifuged. Then, the two categories of extracts (water and sodium hydroxide) are supplemented with 95% ethanol in a proportion of 1:5 by volume. The polysaccharides are then collected by centrifugation and taken up with distilled water at 60° C. The nP are assayed with sulphuric phenol and the aP with meta-phenylphenol. The reference solutions are, respectively, an aqueous solution at 100 mg/l of glucose and 50 mg/l of galacturonic acid for nP and aP.

EXAMPLES

The invention is illustrated by the following examples, without, nevertheless, being limited thereto.

Example 1

8 piles, each of approximately 1 m$^3$, of oak staves stacked in staggered rows, arranged to leave a space between each stave in order to allow the solution to circulate, are immersed in a container containing 15 000 liters of water. The temperature of the water is adjusted to 40° C. and the pH to 4.5–5.0, the wood being left to soak for 24 hours.

Next, 8 kg of an enzymatic formulation are added, comprising mainly:

cellulases (IUB No. EC 3.2.1) with in particular
   an activity measured in endocellulase units (IUB No. EC 3.2.1.4) of 10000 ECU/g of formulation,
   an activity measured in xylanase units (IUB No. EC 3.2.1.8) of 6000 BXU/g of formulation, and
   an activity measured in β-mannanase units (IUB No. EC 3.2.1.78) of 4000 MNU/g of formulation;
α-amylases (IUB No. EC 3.2.1.1) with an activity measured in "α-thermo-stable" units of 10000 $_\alpha$TU/g of formulation.

These concentrations are, of course, given by way of example. It is clear that they may vary considerably depending on the various parameters used for the treatment (treatment time, strength desired, nature of the wood, volume of the bath, volume of wood to be treated, pH and temperature of the bath, etc.).

The enzymatic solution is left to act while maintaining a gentle circulation in order to ensure homogeneous distribution of the enzymes in the bath.

The wood is then treated for 48 hours and then taken out of the bath and transferred to the drying facility for three weeks in order to allow it to attain a water content of approximately 18%. The staves are then ready for the manufacturing of barrels, after a total treatment of 24 days instead of 2 years in the case of natural ageing, for a final organoleptic quality which is equivalent. The drying, will, however, have to be adjusted for each batch of wood in order to avoid the appearance of cracks.

Example 2

Sawdust and blocks of oak for cooperage (*Quercus petraea*) were treated with an aqueous solution of enzymes according to Example 1 (1 g of enzymatic preparation in 2.5 l of water per dm$^3$ of wood), for 24 h at 35–40° C. and pH 5, according to the materials and methods above.

After treatment, the main groups of compounds of the wood were fractionated and the various fractions were compared with respect to a nontreated control.

In order to carry out this fractionation, the oak extract is evaporated to dryness. The resulting dry extract is taken up with a volume of water, with stirring for 2 hours at 30° C. The resulting insoluble fraction comprises the lignins. The soluble fraction is again evaporated to dryness. The resulting dry extract is then taken up with a volume of an ethanol/water (9:1 by volume) mixture and stored for 12 h at 4° C. The resulting insoluble fraction comprises the polysaccharides. With regard to the soluble fraction, it comprises the ellagitannins. In the treated wood, the dry extract is 4.2% by weight with respect to the wood, against 12.3% by weight for the green-wood control. The percentages by weight of each of the three fractions, with respect to the dry extract, are given in Table I.

TABLE I

| | Ellagitannins | Polysaccharides | Lignins |
|---|---|---|---|
| Control | 60% | 30% | 10% |
| Treated according to the invention | 35% | 50% | 15% |

This test made it possible to demonstrate hydrolysis of the ellagitannins, in parallel with a relative increase in the polysaccharide content, in the dry extract.

These various fractions were then subjected to more precise assays, demonstrating a decrease in extractable solids, in ellagitannins, in proanthocyanidins and in glucosylated coumarins (see Table II).

TABLE II

| Results in mg/g of wood | Control | Treated according to the invention |
|---|---|---|
| Dry extract on: | | |
| sawdust | 123 | 42 |
| wood* | 73 | 26 |
| Ellagitannins on: | | |
| sawdust | 54 | 21 |
| wood* | 32 | 14 |
| Proanthocyanidins on: | | |
| sawdust | 0.62 | 0.12 |
| wood* | 0.47 | 0.19 |
| Coumarins glucosylated coumarins (esculin + scopolin) on: | | |
| sawdust | 5.7 | 1.4 |
| wood* | 3.2 | 1.1 |
| aglucone coumarins (esculetin + scopoletin) on: | | |
| sawdust | 1.3 | 6.8 |
| wood* | 4.8 | 7.1 |

*Size of the samples: 5 cm × 5 cm × 10 cm

A substantial increase in the polysaccharides was also noted in another test in which the assay made it possible to distinguish between the nP and aP polysaccharides (see Table III).

TABLE III

| | Soluble polysaccharides (mg/g of wood) | |
|---|---|---|
| | Neutral (nP) | Acid (aP) |
| Control | 370 | 25 |
| Treated according to the invention | 625 | 48 |

The treatment therefore makes it possible to eliminate certain substances judged to be undesirable due to their astringent nature (such as castalagin) or bitter nature (such as esculin), and to transform them into neutrally tasting molecules (such as gallic acid, ellagic acid and, to a lesser degree, esculetin), and also to increase the polysaccharide content (which will tend to make wine matured in the presence of this wood fuller and fatter).

A series of taste tests were also carried out (see Table IV). They confirm the above experiments in that the amount of wood required to detect the bitter or astringent natures are much higher in the case of the wood treated enzymatically according to the invention, with respect to green wood dried artificially or naturally.

TABLE IV

Comparison of the taste detection thresholds as a function of the method of seasoning the wood, indicating the taste detection threshold ($T_{50\%}$)* in mg/l of wine model solution

| | Astringency | Bitterness |
|---|---|---|
| Green wood | 130 | 110 |
| Wood seasoned | | |
| according to the invention | 420 | 350 |
| by natural drying | 300 | 290 |
| by artificial drying (drying facility) | 165 | 140 |

*$T_{50\%}$: concentration starting from which a substance is detected by 50% of the tasters.

Example 3

The measurement of phenol heterosidase enzymatic activity PeH is based on the release of carboxylic functions which lower the pH of the reaction medium. 9 mg of an aqueous extract of green oak are added, in a test tube, to 9 ml of a 0.1 M NaCl solution, pH 4.5, containing 1% of enzymatic preparation EP. A control tube is prepared under the same conditions, without enzymes. The pH is measured in the two tubes at time 0 ($pHc_0$ for the control and $pHe_0$ for the enzyme) and after 4 hours of incubation at 25° C. ($pHc_4$ and $pHe_4$, respectively). The optimum conditions were established beforehand and there is perfect correlation between the release of glucose and the drop in pH.

The phenol heterosidase activity is calculated from the equation:

$$PeH=[(pHc_0-pHc_4)-(pHe_0-pHe_4)/4]\times 100$$ (PeH being expressed in $10^{-3}$ units of pH/ml/h)

The activity measurements were carried out on various species of oak treated according to Example 2, in order to determine the differences in possible effectiveness of the enzymatic formulation, as a function of the species of oak (see Table V).

TABLE V

| | Phenol heterosidase activity | | | | | | |
|---|---|---|---|---|---|---|---|
| | Vosges | Allier | Limousin | Q. alba | Q. stellata | Q. lobata | Q. prinus |
| PeH | 2.5 | 2.7 | 1.9 | 4.6 | 4.3 | 4.7 | 4.9 |
| ($10^{-3}$ | 3.2 | 2.4 | 3.3 | 4.2 | 4.8 | 4.9 | 4.5 |
| pH/ml/ | 2.8 | 3.6 | 3.5 | 3.9 | 4.3 | 4.5 | 4.7 |
| h) | 3.4 | 2.2 | 2.4 | 4.5 | 4.7 | 4.6 | 4.7 |
| | 4.5 | 2.5 | 3.5 | 4.5 | 4.5 | 4.7 | 4.8 |
| Means | 3.3 | 2.6 | 2.9 | 4.3 | 4.5 | 4.7 | 4.7 |

With regard to the French oaks (Vosges, Allier, Limousin), no significant difference is observed, the composition of the extracts being, itself, often similar.

In the species of American oaks (Q. alba, stellata, lobata, prinus) it is noted that the activity is expressed more strongly than in the French oaks. This is doubtless due to the presence of galloyl-containing compounds, which are present in greater amounts. Since the activity is greater, more significant seasoning of the American species may therefore be expected, which, in terms of taste, should bring them closer to the French species. This tendency is confirmed during tastings.

TABLE VI

Inhibition of the phenol heterosidase activity by phenol compounds

| | Ellagitannin (vescalagin) reference solution | With galloy-tannins at the concentration of | With procyanidins at the concentration of | | |
|---|---|---|---|---|---|
| PeH | 1 g/l | 1 g/l | 0.1 g/l | 0.5 g/l | 1 g/l |
| $10^{-3}$ pH/ml/h | 100 | 260 | 80 | 30 | 0 |

In general, all the heteroside substrates are used by the enzymatic activities present. Only the condensed tannins from grape show inhibition of the phenol heterosidase activity. This effect is demonstrated in Table VI, by a decrease in PeH with respect to vescalagin.

Not only does the enzymatic preparation not act on the procyanidins (tannins from grape and from wine), but it is also greatly inhibited by them. It may be concluded from this that a possible (but highly unlikely) residual phenol heterosidase activity in the cask will not modify the tannic qualities of the wine, developed by the grape.

The condensed tannins of the grape in fact have the property of combining proteins, which explains the inactivation of the activities of our enzymatic solution. This inhibition is irreversible since, when the enzymatic solution is returned to a situation in which condensed tannins are absent, it does not recover its initial activity.

TABLE VII

Influence of the ellagitannin concentration on the phenol heterosidase activity

| Concentration (g/l) | 1 | 1.5 | 2 | 3 | 4 | 5 |
|---|---|---|---|---|---|---|
| PeH ($10^{-3}$ pH/ml/h) | 2.7 | 2.2 | 0.4 | 0.1 | 0.08 | 0 |

The activity is inhibited on media which are too rich in pure ellagitannins, as indicated in Table VII. In practice, when wood is treated, this does not represent a limitation of the technique since the local concentration of free ellagitannins never reaches these values. The ellagitannins of the wood are in fact associated with glucoside structures which attach them to the walls of the fibres. The immobilized form of these tannins does not, itself, show any inhibition on the phenol heterosidase activity. As these structures are digested by the enzymatic preparation, the ellagitannins are released into the medium, but are immediately hydrolysed by the enzymes present.

In addition, applying the enzymatic preparation by soaking enables the wood to be washed, depleting the superficial layers and thus decreasing, accordingly, the local concentration of ellagitannins.

TABLE VIII

Influence of pH on the phenol heterosidase activity

| pH | 2 | 3 | 4 | 5 | 6 |
|---|---|---|---|---|---|
| PeH ($10^{-3}$ pH/ml/h) | 0.6 | 1.5 | 2.5 | 3.2 | 2.8 |

As indicated in Table VIII, the phenol heterosidase activity is optimal at pH 5, which corresponds to the general optimum of activity of the enzymatic preparation, measured by the release of glucose into the medium.

TABLE IX

Enhancement of the value of chestnut through the use of the enzymatic preparation according to the invention

| Results in mg/g | Digallic acid | Glucosylated coumarins |
|---|---|---|
| | Control | |
| Dordogne chestnut | 10.2 | 8.3 |
| Dauphiné chestnut | 9.3 | 5.7 |
| Gironde chestnut | 4.6 | 10.2 |
| | Treated according to the invention | |
| Dordogne chestnut | <0.1 | 2.3 |
| Dauphiné chestnut | 0.4 | 1.7 |
| Gironde chestnut | 0.8 | 3.5 |

Chestnut extracts (rich in digallic acid) from diverse origins were subjected (see Table IX) to enzymatic hydrolysis with the enzymatic preparation according to Example 2. Virtually total hydrolysis of the digallic acid to gallic acid emerges from this, and also a large decrease in the glucosylated coumarins (the aglucone coumarins being insipid).

These results are of great importance since they show the possibility of enhancing the value of a species which has been used very little to date. Chestnut in fact has all the mechanical qualities required for making cooperage wood, but is used very little because of the considerable bitterness which it produces.

The enzymatic treatment very greatly decreases this bitterness and makes it possible to envisage chestnut being used more in cooperage, for specific uses in which oak is not suitable. Thus, for maturing colourless spirits, chestnut is absolutely indicated because, since it has no ellagitannins, it will hardly modify the fruit taste of the alcohol and, since it has no pigments, neither will it colour the alcohol left to mature in these casks.

What is claimed is:

1. A method for seasoning green wood intended to come into contact with food, and comprising a step of bringing the wood to be treated into contact with a bath comprising isolated enzymes of the IUB hydrolase class, wherein the bath contains IUB hydrolase class enzymes selected from the group consisting of α-amylases (3.2.1.1), cellobiohydrolases (3.2.1.91), endocellulases (3.2.1.4), endoglucanases (3.2.1.4), β-glucosidases (3.2.1.21), hemicellulases (3.2.1.4), xylanases (3.2.1.8), and β-mannanases (3.2.1.78).

2. The method according to claim 1, wherein the wood is brought into contact with the bath by immersing the wood for a period of time ranging from about 30 minutes to about 2 weeks.

3. The method according to claim 1, wherein the bath has a pH in the range of about 3 to about 8.

4. The method according to claim 1 wherein the bath has a temperature in the range of about 20 to about 70° C.

5. The method according to claim 1, further comprising a step of adjusting the water content of the wood to be treated to a value in the range of about 25 to about 45% by weight before bringing the wood into contact with the bath.

6. A method for seasoning green wood intended to come into contact with food, and comprising the steps of contacting the wood to be treated with a bath comprising isolated enzymes of the IUB hydrolase class, and subsequently artificially drying the wood; wherein the enzymes are selected from the group consisting of α-amylases (3.2.1.1), cellobiohydrolases (3.2.1.91), endocellulases (3.2.1.4), endoglucanases (3.2.1.4), β-glucosidases (3.2.1.21), hemicellulases (3.2.1.4), xylanases (3.2.1.8), β-mannanases (3.2.1.78), and combinations thereof.

7. The method of claim 6, including the additional step of adjusting the water content of the wood to be treated to a value in the range of about 25 to about 45% by weight before contacting the wood with the enzymatic bath.

8. The method of claim 6, wherein the contacting is by immersing the wood for a period of time in the range of about 30 minutes to about 2 weeks.

9. The method of claim 6, including the additional step of maintaining the pH of the bath in the range of about 3 to about 8.

10. The method of claim 6, including the additional step of maintaining the temperature of the bath in the range of about 20 to about 70° C.

11. The method of claim 6, wherein the wood is selected from the group consisting of heartwood of oak and heartwood of chestnut.

12. The method of claim 6, wherein the bath contains an endocellulase at an activity in the range of about $1 \times 10^6$ to about $100 \times 10^6$ ECU per $m^3$ of wood to be treated.

13. The method of claim 6, wherein the bath contains a xylanase at an activity in the range of about $0.6 \times 10^6$ to about $60 \times 10^6$ BXU per $m^3$ of the wood to be treated.

14. The method of claim 6, wherein the bath contains a β-mannanase at an activity in the range of about $0.4 \times 10^6$ to about $40 \times 10^6$ MNU per $m^3$ of the wood to be treated.

15. The method of claim 6, wherein the bath contains an α-amylase at an activity in the range of about $1 \times 10^6$ to about $100 \times 10^6$ αTU per $m^3$ of the wood to be treated.

16. The method of claim 6, wherein the bath further comprises enzymes selected from the group consisting of peroxidases, lipases, and combinations thereof.

17. A method of modifying the aromatic characteristics of wood intended to come into contact with food, and comprising the steps of contacting wood to be treated with a bath comprising isolated IUB hydrolase class enzymes selected from the group consisting of α-amylases (3.2.1.1), cellobiohydrolases (3.2.1.91), endocellulases (3.2.1.4), endoglucanases (3.2.1.4), β-glucosidases (3.2.1.21), hemicellulases (3.2.1.4), xylanases (3.2.1.8), β-mannanases (3.2.1.78), and combinations thereof; and subsequently artificially drying the wood; wherein the temperature of the bath is in the range of about 20 to about 70° C.; the pH of the bath is in the range of about 3 to about 8; and the contacting reduces the ellagitannin content of wood, relative to the ellagitannin content of untreated wood.

18. The method of claim 17, wherein the activity of α-amylase, when present, is in the range of about $1 \times 10^6$ to about $100 \times 10^6$ αTU per $m^3$ of the wood to be treated, the activity of endocellulase, when present, is in the range of about $1 \times 10^6$ to about $100 \times 10^6$ ECU per $m^3$ of wood to be treated, the activity of xylanase, when present, is in the range of about $0.6 \times 10^6$ to about $60 \times 10^6$ BXU per $m^3$ of wood to be treated, and the activity of β-mannanase, when present, is in the range of about $0.4 \times 10^6$ to about $40 \times 10^6$ MNU per $m^3$ of the wood to be treated.

* * * * *

UNITED STATES PATENT AND TRADEMARK OFFICE
CERTIFICATE OF CORRECTION

| | | |
|---|---|---|
| PATENT NO. | : 6,623,953 B1 | Page 1 of 1 |
| APPLICATION NO. | : 09/869656 | |
| DATED | : September 23, 2003 | |
| INVENTOR(S) | : Olivier Henry | |

It is certified that error appears in the above-identified patent and that said Letters Patent is hereby corrected as shown below:

On the Title Page, in item (12), "Olivier" should read -- Henry --.

On the Title Page, in item (75), "Henry Olivier, Wavre (BE)" should read -- Olivier Henry, Wavre (BE) --.

Signed and Sealed this

Eighteenth Day of May, 2010

David J. Kappos
*Director of the United States Patent and Trademark Office*